(12) United States Patent
Gilbert et al.

(10) Patent No.: US 6,337,326 B1
(45) Date of Patent: Jan. 8, 2002

(54) N-ARYL-(HOMOPIPERAZINYL)-CYCLOHEXYL AMINES

(75) Inventors: Adam M. Gilbert, Congers, NY (US); Richard E. Mewshaw, King of Prussia, PA (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/706,640

(22) Filed: Nov. 6, 2000

Related U.S. Application Data
(60) Provisional application No. 60/240,938, filed on Nov. 8, 1999.

(51) Int. Cl.[7] .................. C07D 403/08; C07D 403/14; A61K 31/404
(52) U.S. Cl. .................. 514/211.08; 540/575
(58) Field of Search ........ 540/575; 514/211.08

(56) References Cited

U.S. PATENT DOCUMENTS

| | | | |
|---|---|---|---|
| 5,081,246 A | 1/1992 | Hidaka et al. | 544/363 |
| 5,216,150 A | 6/1993 | Hidaka et al. | 540/597 |
| 5,244,895 A | 9/1993 | Hidaka et al. | 514/253 |
| 5,245,034 A | 9/1993 | Hidaka et al. | 546/149 |

FOREIGN PATENT DOCUMENTS

| | | |
|---|---|---|
| EP | 513 691 | 1/1995 |
| EP | 666 258 | 7/1996 |
| WO | WO 97/44329 | 11/1997 |
| WO | WO-00/40554 | * 7/2000 |

OTHER PUBLICATIONS

Wagaw et al J. Org. Chem. 61 (1996) 7240–7241.*
Wolfe et al Acc. Chem. Res. 31 (1998) 805–818.*
Wustrow et al., J. Med. Chem., 1997, vol. 40, pp 250–259.

* cited by examiner

*Primary Examiner*—John M. Ford
(74) *Attorney, Agent, or Firm*—Joseph M. Mazzarese

(57) ABSTRACT

This invention provides novel compounds and methods and compositions using them in the treatment of central nervous system disorders, including depression and anxiety, the compounds having the formula:

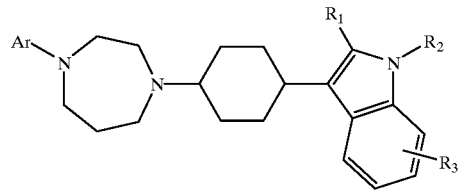

wherein Ar is an aryl group of 4 to 10 carbon atoms or a heteraryl group of 4 to 10 carbon atoms; $R_1$ and $R_2$ are independently selected from hydrogen, straight chain alkyl of 1 to 12 carbon atoms, branched alkyls of 3 to 10 carbon atoms or cycloalkyl of 3 to 10 carbon atoms; $R_3$ is H, straight chain, branched or cyclic alkyl, halogen, alkoxy, haloalkyl, OH, nitro, nitrile, amino, CN, carboxy, alkoxycarbonyl, alkylcarbonyl, aminocarbonyl and alkylaminocarbonyl; or a pharmaceutically acceptable salt thereof.

19 Claims, No Drawings

N-ARYL-(HOMOPIPERAZINYL)-CYCLOHEXYL AMINES

This application claims the benefit of U.S. Provisional Application No. 60/240,938, filed Nov. 8, 1999.

The present invention relates to N-aryl-homopiperazinyl-cyclohexylamine derivatives having pharmacological activity, and to their use in the treatment of diseases affected by disorders of the serotonin affected neurological systems, such as depression and anxiety.

BACKGROUND OF INVENTION

Pharmaceuticals with enhance serotonergic neurotransmission are of useful benefit for the treatment of many psychiatric disorders, including depression and anxiety. The first generation of non-selective serotonin-affection drugs operated through a variety of physiological functions which endowed them with several side effect liabilities. The more currently prescribed drugs, the selective serotonin reuptake inhibitors (SSRIs), act predominately by inhibiting 5-HT which is released at the synapses, from being actively removed from the synaptic cleft via a presynaptic serotonin transport carrier.

Wustrow et al. have disclosed a series of 3-[[4-aryl-1-piperazinyl)alkyl]cyclohexyl]-1H-indoles as dopamine $D_2$ partial agonists in *J. Med. Chem.* 1997, 40, 250.

Cipollina et al. have disclosed a series of indolylcycloalkylamines as serotonergic vasoconstrictors for the treatment of vascular or migraine headaches in European Patent Application EP 666258.

Shiota et al. have disclosed a series of cyclic diarylalkyl derivatives (including aryl homopiperazines) as chemokine receptor antagonists in PCT Int. Patent Application WO 9744329. Hidaka et al. have disclosed a series of aryl cyclic diamines (including aryl homopiperazines) as anti-ulcer agents in U.S. Pat. No. 5,244,895 and European Patent Application 513691. Hidaka et al. have also disclosed a series of aryl cyclic diamines (including aryl homopiperazines) as blood vessel relaxants in U.S. Pat. Nos. 5,081,246; 5,216,150 and 5,245,034.

DESCRIPTION OF THE INVENTION

The present invention provides N-aryl-homopiperazinyl-cyclohexylamine derivatives having pharmacological activity as 5-HT transporters, and to their use in the treatment of diseases affected by disorders of the serotonin affected neurological systems, such as depression and anxiety.

In accordance with this invention there, is provided a group of compounds represented by the formula I:

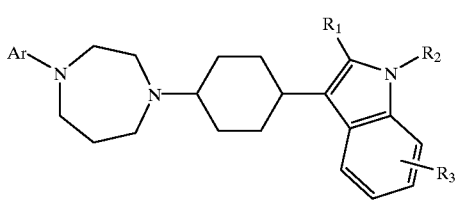

I wherein:
Ar is an aryl group of 4 to 10 carbon atoms or a heteroaryl group of 4 to 10 carbon atoms, the aryl or heteroaryl group being optionally substituted by from 1 to 3 groups selected from alkyl of 1 to 6 carbon atoms, alkoxy of 1 to 6 carbon atoms, thioalkyl of 1 to 6 carbon atoms, perfluoralkyl of 1 to 6 carbon atoms, hydroxy, nitro, amino, or cyano;

$R_1$ and $R_2$ are independently, hydrogen, straight chain alkyls of 1 to 12 carbon atoms, branched alkyls of 3 to 10 carbon atoms or cycloalkyls of 3 to 10 carbon atoms;

$R_3$ is H, straight chain alkyl of 1 to 12 carbon atoms, branched alkyl of 3 to 10 carbon atoms, cycloalkyl of 3 to 10 carbon atoms, halogen, alkoxy group of 1 to 12 carbon atoms, haloalkyl of 1 to 12 carbon atoms, hydroxy, nitro, nitrile, amino, cyano, carboxy, alkoxycarbonyl of 1 to 12 carbon atoms, alkylcarbonyl of 1 to 12 carbon atoms, aminocarbonyl and alkylaminocarbonyl of 1 to 12 carbon atoms; and all crystalline forms or a pharmaceutically acceptable salt thereof.

Among the preferred compounds of this invention are those of formula I wherein:
Ar is an aryl group of 5 or 6 carbon atoms or a heteroaryl group of 5 to 10 carbon atoms;

$R_1$ and $R_2$ are independently, H, straight chain alkyls of 1 to 8 carbons or branched alkyls of 3 to 8 carbon atoms;

$R_3$ is H, straight chain alkyl of 1 to 8 carbon atoms, branched alkyl of 3 to 6 carbon atoms, cycloalkyl of 3 to 8 carbon atoms, halogen, alkoxy of 1 to 6 carbon atoms, haloalkyl of 1 to 6 carbon atoms, haloalkoxy or 1 to 6 carbon atoms, hydroxy, nitro, nitrile, amino, cyano, carboxy, alkoxycarbonyl of 1 to 6 carbon atoms, alkylcarbonyl of 1 to 6 carbon atoms, aminocarbonyl and alkylaminocarbonyl of 1 to 6 carbon atoms;

and all crystalline forms or a pharmaceutically acceptable salt thereof.

In still more preferred aspects of the invention are provided compounds of formula I wherein:
Ar is an aryl group of 6 carbon atoms or a heteroaryl group or a heteroaryl group of 5 to 10 carbon atoms;

$R_1$ and $R_2$, are independently, H, straight chain alkyls of 1 to 3 carbons or branched alkyls of 3 to 6 carbon atoms;

$R_3$ is H, halogen, cyano $CONH_2$, or $CO_2H$;
and all crystalline forms or a pharmaceutically acceptable salt thereof.

Alkyl, whether used alone or as part of another group include straight and branched chain alkyl groups containing from 1 to 12 carbon atoms. For example, methyl, ethyl, propyl, isopropyl, butyl, i-butyl and t-butyl are encompassed by the term alkyl. In some embodiments of the present invention alkyl may refer to substituted or unsubstituted alkyl. Carbon number refers to carbon backbone and does not include carbon atoms of substituents such as alkoxy substitutions and the like. Halogen, as used herein means chlorine, bromine, iodine and fluorine.

Aryl, as used herein refers to single or multiple 4 to 10 membered aromatic ring radicals including but not limited to phenyl, benzyl, naphthalene, anthracene, phenanthrene, indene and indacene. Preferred are phenyl, benzyl and naphthalene. In some embodiments of the present invention, the aryl group may be substituted by alkyl groups, perfluoroalkyl groups, preferably trifluoromethyl groups, alkoxy groups, and halogens.

Heteroaryl as used herein refers to single or multiple 4 to 10 membered aromatic ring radicals having from 1 to 3 heteroatoms selected from S, O or N including, but not limited to, furan, thiophene, pyrrole, imidazole, oxazole, thiazole, isoxazole, pyrazole, isothiazole, oxadiazole, triazole, thiadiazole, quinolizine, quinoline, isoquinoline, cinnoline, phthalazine, quinazoline, quinoxaline, napthyridine, pteridine, pyridine, pyrazine, pyrimidine, pyridazine, pyran, triazine, indole, isoindole, indazole, indolizine, and isobenzofuran. Preferred heteroaryls include furan, thiophene, pyrrole, imidazole, oxazole, thiazole, isoxazole, pyrazole, isoxazole, isothiazole, oxadiazole, triazole, thiadiazole, quinolizine, quinoline, and isoquinoline. More preferred heteroaryls include furan, thiophene, imidazole, isoxazole, quinoline and pyrazole. In some embodiments of the present invention, the heteroaryl group is substituted.

Preferably, the substituted aryl group is substituted with from 1 to 3 groups. The substituted heteroaryl group is preferably substituted with 1 to 3 groups and more preferably 1 to 2 groups. Alkyl and cycloalkyl groups may also be substituted. Suitable substitutions include, but are not limited to halogen, alkyl, alkoxy, haloalkyl, haloalkoxy, hydroxy, nitro, nitrile, amino, cyano, carboxy, alkoxycarbonyl, alkylcarbonyl, alkoxycarbonylalkyl and alkylcarbonyloxy.

Among the most preferred compounds of the present invention are:
3-{4-[4-(2-Methoxy-phenyl)-[1,4]diazepan-1-yl]-cyclohexyl}-1H-indole;
8-{4-[4-(1H-Indol-3-yl)-cyclohexyl-]-[1,4]diazepan-1-yl}-quinoline;
3-{4-[4-(2-Methoxy-phenyl)-[1,4]diazepan-1-yl]-cyclohexyl}-5-fluoro-1H-indole;
3-{4-[4-(2-Methoxy-phenyl)-[1,4]diazepan-1-yl]-cyclohexyl}-5-cyano-1H-indole;
3-{4-[4-(2-Methoxy-phenyl)-[1,4]diazepan-1-yl]-cyclohexyl}-6-fluoro-1H-indole;
8-{4-[4-(5-Fluoro-1H-indol-3-yl)-cyclohexyl]-[1,4]diazepan-1-yl}-quinoline;
8-{4-[4-(5-Cyano-1H-indol-3-yl)-cyclohexyl]-[1,4]diazepan-1-yl}-quinoline;
8-{4-[4-(6-Fluoro-1H-indol-3-yl)-cyclohexyl]-[1,4]diazepan-1-yl}-quinoline;
3-{4-[4-(3-Trifluoromethyl-phenyl)-[1,4]diazepan-1-yl]-cyclohexyl}-5-fluoro-1H-indole;
3-{4-[4-(3-Trifluoromethyl-phenyl)-[1,4]diazepan-1-yl]-cyclohexyl}-5-cyano-1H-indole;
3-{4-[4-(3-Trifluoromethyl-phenyl)-[1,4]diazepan-1-yl]-cyclohexyl}-6-fluoro-1H-indole;
or a pharmaceutically acceptable salt of one of these compounds.

It is understood that the definition of the compounds of formula I, when $R_1$, $R_2$ or $R_3$ contain asymmetric carbons, encompass all possible stereoisomers and mixtures thereof which possess the activity discussed below. In particular, it encompasses racemic modifications and any optical isomers which possess the indicated activity. Optical isomers may be obtained in pure form by standard separation techniques.

Pharmaceutically acceptable salts are those derived from such organic and inorganic acids as: lactic, citric, acetic, tartaric, succinic, maleic, malonic, oxalic, fumaric, hydrochloric, hydrobromic, phosphoric, nitric, sulfuric, methanesulfonic, and similarly known acceptable acids. Where $R_1$, $R_2$ or $R_4$ contain a carboxyl group, salts of the compounds of this invention may be formed with bases such as alkali metals (Na, K, Li) or the alkaline earth metals (Ca or Mg).

As mentioned previously, the compounds of formula I have affinity for the 5-HT reuptake transporter and are useful in the treatment of diseases affected by disorders of the serotonin affected neurological systems, such as depression and anxiety, sleep disorders, sexual dysfunction, alcohol and cocaine addiction, cognition enhancement and related problems. The present invention accordingly also provides pharmaceutical compositions which comprise a compound of this invention in combination or association with a pharmaceutically acceptable carrier or excipient.

The compositions are preferably adapted for oral or subcutaneous administration. However, they may be adapted for other modes of administration.

The compositions of the invention may be formulated with conventional excipients, such as a filler, a disintegrating agent, a binder, a lubricant, a flavoring agent and the like. They are formulated in conventional manner, for example, in a manner similar to that use for known antihypertensive agents, diuretics and β-blocking agents. Applicable solid carriers or excipients can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

In order to obtain consistency of administration, it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

Generally, the compounds of formula I are conveniently synthesized as described below:

In accordance with the present invention, compounds of formula I may be prepared to the following Scheme I.

Scheme I

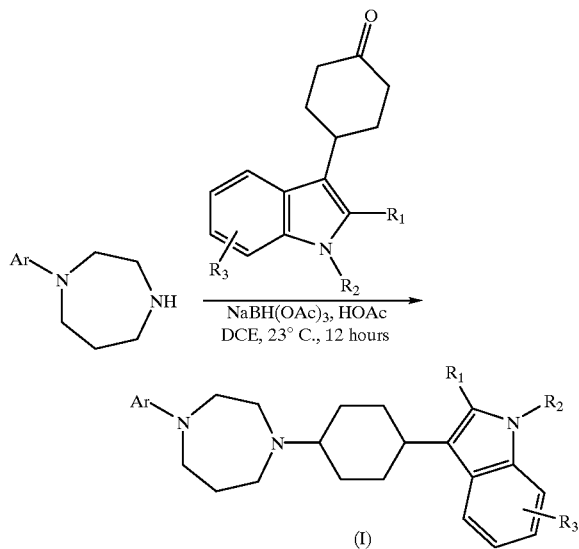

Thus, compound of formula II is reacted with compound of formula III, acetic acid in dichloroethane at 23° C. to give a compound of formula I in accordance with the procedure described by Abdel-Magid, Carson, Harris, Maryanoff and Shah in *J. Org. Chem.* 1996, 61, 3849.

In accordance with the present invention, compounds of formula II may be prepared to the following Scheme II.

Scheme II

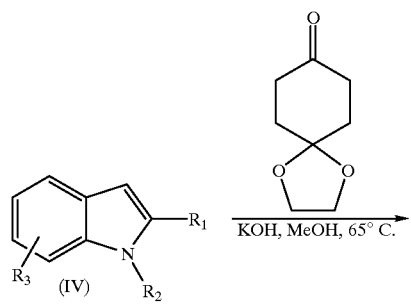

-continued

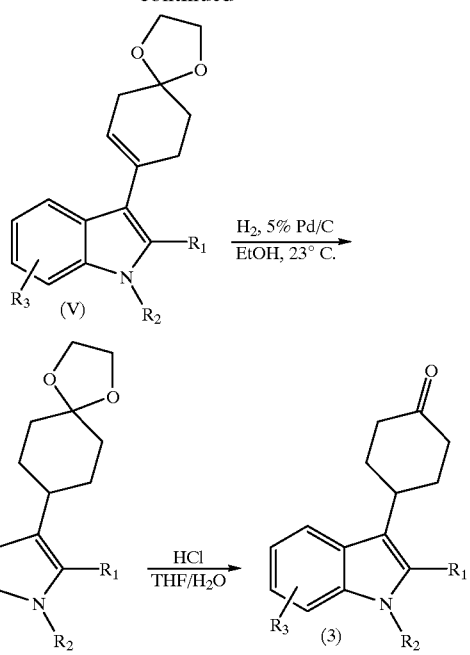

Thus compounds of formula IV are reacted with 1,4-cyclohexanedione monoethylene ketal, potassium hydroxide in methanol at 65° C. to give compounds of formula V as described by Wustrow et al. in *J. Med. Chem.* 1997, 40, 250. Hydrogenation to compounds of formula VI can be realized by treatment in suitable solvents such as an alcohol, but not limited to EtOH with $H_2$ and 5% Pd/C. Hydrolysis to compounds of formula III can be carried out using 1N HCl in a 1:1 mixture of THF and water.

In accordance with the present invention, compounds of formula II may be prepared to the following Scheme III.

Scheme III

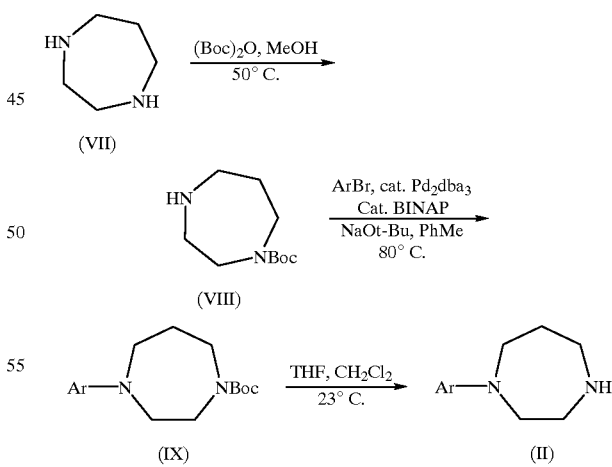

Thus the compound of formula VII is treated with (Boc)$_2$O in a suitable solvent such as chloroform, THF or an alcohol, but not limited to MeOH to give the compound of formula VII. Conversion to compounds of formula IX can be realized by treatment with an aryl bromide, catalytic Pd$_2$dba$_3$, catalytic BINAP, NaOt-Bu, in toluene at 80° C. according to the procedure of Buchwald et al. in *Anew.*

*Chem., Int. Ed. Engl.* 1995, 34, 1348. Deprotection to give compounds of formula II can be accomplished via treatment with TFA in $CH_2Cl_2$ at 23° C.

The present invention further provides a compound of the invention for use as an active therapeutic substance. Compounds of formula (I) are of particular use in the treatment of diseases affected by disorders of the serotonin.

The present invention further provides a method of treating depression and anxiety in mammals including man, which comprises administering to the afflicted mammal an effective amount of a compound or a pharmaceutical composition of the invention.

The following examples are presented to illustrate rather than limit the present invention.

EXAMPLES

The 5-HT transporter affinity of the compounds of this invention was established in accordance with standard pharmaceutically accepted test procedures with representative compounds as follows:

Rat Brain $^3$H-Paroxetine Binding Assay (RB 5HT Transporter)

The following assay was used to determine a compound's affinity of the 5-HT transporter.

A protocol similar to that used by Cheetham et. al. (*Neuropharmacol.* 1993, 32, 737) was used. Briefly, frontal cortical membranes prepared from male S.D. rats were incubated with $^3$H-parxetine (0.1 nM) for 60 min. at 25° C. All tubes also contained either vehicle, test compound (one to eight concentrations), or a saturating concentration of fluoxetine (10 $\mu$M) to define specific binding. All reactions are terminated by the addition of ice cold Tris buffer followed by rapid filtration using a Tom Tech filtration device to separate bound from free $^3$H-paroxetine. Bound radioactivity was quantitated using a Wallac 1205 Beta Plate® counter. Nonlinear regression analysis was used to determine $IC_{50}$ values which were converted to $K_i$ values using the method of Cheng and Prusoff (*Biochem. Pharmacol.* 1973, 22, 3099);

$$K_i = \frac{IC_{50}}{\text{Radioligand concentration}/(1 + KD)}$$

Inhibition of $^3$H-5-HT Uptake by cells Possessing the Human 5-HT Transporter (HC 5-HT Transporter)

A human carcinoma cell line (Jar cells) possessing low endogenous levels of the 5-HT-transporter are seeded into 96 well plates and treated with staurosporine at least 18 h prior to assay. [Staurosporine greatly increases the expression of the 5-HT-transporter.] On the day of assay, vehicle, excess of fluoxetine, or test compound is added to various wells on the plate. All wells then receive $^3$H-5-HT and are incubated at 37° C. for 5 min. The wells are then washed with ice cold 50 mM Tris HCl (pH 7.4) buffer and aspirated to remove free $^3$H-5-HT. 25 $\mu$l of 0.25 M NaOH is then added to each well to lyse the cells and 75 $\mu$l scintillation cocktail (Microscint™ 20) added prior to quantitation on a Packard TopCount machine. Tubes with vehicle represent total possible uptake, radioactivity counted in tubes with fluoxetine represent nonspecific binding/uptake and is subtracted from the total possible uptake to give total possible specific uptake. This nonspecific binding (usual low in number) is then subtracted from the counts obtained in wells with various test compounds (or different concentrations of test drug) to give specific uptake in the presence of drug. Specific uptake is then expressed as a % of control values and is analyzed using nonlinear regression analysis (Prizm) to determine $IC_{50}$ values. If the compound is active at inhibiting 5-HT uptake, its counts will be close to that obtained with fluoxetine.

Results from these two assays are presented below in Table I.

TABLE I

| Compound | n | RB 5-HT Transporter $K_i$ (nM) | HC 5-HT Transporter $IC_{50}$ (nM) |
|---|---|---|---|
| Example 1 | 1 | 42.0 | 578 |
| Example 2 | 1 | 9.0 | 399 |
| Example 3 | 1 | 12.0 | 1144 |
| Example 4 | 1 | 27.0 | — |
| Example 5 | 1 | 4.9 | 272 |
| Example 6 | 1 | 9.0 | 602 |
| Example 7 | 1 | 11.0 | — |
| Example 8 | 1 | 2.7 | 317 |
| Example 9 | 1 | 86.0 | 4470 |
| Example 10 | 1 | 207 | 3765 |
| Example 11 | 1 | 27.0 | 1284 |

Hence the compounds of this invention have substantial affinity for the 5-HT transporter and are useful in the treatment of diseases affected by disorders of the serotonin affected neurological systems, such as depression and anxiety, by administration orally, parenterally, or by aspiration to a patient in need thereof.

Example 1

3-{4-[4-(2-Methoxy-phenyl)-[1,4]diazepan-1-yl]-cyclohexyl}-1H-indole

Step 1

3-(1,4-Dioxa-spiro[4.5]dec-7-en-8-yl)-1H-indole

Indole (22.6 g, 190 mmol), 1,4-cyclohexanedione monoethylene ketal (22.8 g, 145 mmol) and KOH (4.6 g, 80 mmol) were heated to reflux in 50 mL of MeOH for 6 h. The reaction mixture was cooled to 23° C., a solid precipitated and was collected by vacuum filtration. This solid was washed with 3×30 mL of $H_2O$ to give 33.3 g (130.5 mmol, a 90% yield) of the title compound as a white solid. MS (ES) m/z (relative intensity): 256 ($M^+$+H, 100).

Step 2

3-(1,4-Dioxa-spiro[4.5]dec-8-yl)-1H-indole

A mixture of 3-(1,4-dioxa-spiro[4.5]dec-7-en-8-yl)-1H-indole (10.0 g, 39.2 mmol) and 10% Pd/C (1.0 g) in 100 mL of EtOH was placed under 40 psi of $H_2$ and shaken at 23° C. for 3 h. The Pd/C was removed via filtration, and the solvent evaporated. Flash chromatography ($CH_2Cl_2$/MeOH) gave 8.66 g (33.7 mmol, an 86% yield) of the title compound as a white solid. MS (ES) m/z (relative intensity): 258 ($M^+$+H, 100).

Step 3

4-(1H-Indol-3-yl)-cyclohexanone

To a 23° C. solution of 8.66 g (33.7 mmol) 3-(1,4-dioxa-spiro[4.5]dec-8-yl)-1H-indole and 200 mL THF was added 200 mL of 1N HCl. After stirring for 12 h, the organics were evaporated and the resulting slurry was extracted with 2×150 mL EtOAc. The combined organics were washed with 2×100 mL of 1N NaOH, dried over $MgSO_4$, filtered and evaporated to an off-white solid. Flash chromatography on silica gel, eluting with hexanes/EtOAc (1/1) gave 5.89 g (27.6 mmol, an 82% yield) of the title compound as a white solid. mp 123–125° C.; MS (ES) m/z (relative intensity): 214 ($M^++H$, 100).

Step 4

[1,4]Diazepane-1-carboxylic acid tert-butyl ester

To 5.0 g (50 mmol) of homopiperazine in 200 mL MeOH at 0° C. was added a solution of 11.93 g (54.7 mmol) of $(Boc)_2O$ and 100 mL MeOH in drops over 1 h. The mixture was warmed to 23° C. and then warmed to 50° C. for 3 h. After cooling to 23° C., the resulting reaction mixture was filtered through Celite and the solvent was evaporated to a volume of 100 mL. This solution was extracted with 3×100 mL of 1N citric acid, the combined aqueous layers are washed with 1×100 mL EtOAc and then the aqueous solution was basified to pH=11 with solid $Na_2CO_3$. The resulting slurry was extracted with 3×100 mL EtOAc, the combined organics were dried over $Na_2SO_4$, filtered and evaporated to give 3.2 g (15.9 mmol, a 32% yield) of the title compounds as a light yellow oil. $^1H$ NMR (300 MHz, $CDCl_3$): δ1.46 (s, 9H), 1.70–1.85 (m, 2H), 2.81–2.96 (m, 4H), 3.37–3.53 (m, 4H); IR (KBr, $cm^{-1}$): 3348w, 1960s; MS (ES) m/z (relative intensity): 201 ($M^++H$, 100).

Step 5

4-(2-Methoxy-phenyl)-[1,4]diazepane-1-carboxylic acid tert-butyl ester

To 1.6 g (7.99 mmol) [1,4]diazepane-1-carboxylic acid tert-butyl ester was added 1.09 mL (1.64 g, 8.79 mmol) of 2-bromoanisole, 37 mg (0.04 mmol) of $Pd_2dba_3$, 75 mg (0.12 mmol) of (±)-BINAP, 1.08 g (11.19 mmol) of NaOt-Bu, 20 mL of toluene and resulting slurry was heated to 80° C. for 20 h. After cooling to 23° C., the reaction mixture was filtered through Celite and evaporated to leave a dark brown oil. Flash chromatography on silica gel, eluting with $CH_2Cl_2$/EtOAc (1/0 to 40/1 to 20/1) gave 2.17 g (7.08 mmol, an 89% yield) of the title compound as a light yellow oil. $^1H$ NMR (300 MHz, $CDCl_3$): δ1.45 and 1.47 (singlets, 9H—rotational isomers), 1.91–2.07 (m, 2H), 3.16–3.31 (m, 4H), 3.47–3.65 (m, 4H), 3.85 (s, 3H), 6.72–6.96 (m, 4H); IR (KBr, $cm^{-1}$):1691s; MS (ES) m/z (relative intensity): 307 ($M^++H$, 100). Anal. Calcd. for $C_{17}H_{26}N_2O_3$: C, 66.64; H, 8.55; N, 9.14. Found: C, 66.18; H 8.54; N, 8.80.

Step 6

1-(2-Methoxy-phenyl)-[1,4]diazepane

To 2.03 g (6.62 mmol) of 4-(2-methoxy-phenyl)-[1,4] diazepane-1-carboxylic acid tert-butyl ester in 30 mL $CH_2Cl_2$ at 23° C. was added 5 mL trifluoroacetic acid. After stirring at 23° C. for 30 min, 4 additional mL of trifluoroacetic acid were added. After a total of 1 h, the reaction solution was poured into 200 mL of saturated aqueous $NaHCO_3$ and extracted with 3×100 mL of EtOAc. The combined organics were washed with 1×200 mL $H_2O$, 1×200 mL brine, dried over $Na_2SO_4$, filtered and evaporated to give 1.01 g (4.90 mmol, a 74% yield) of the title compound as a yellow oil. $^1H$ NMR (300 MHz, $CDCl_3$): δ1.99 (pent, J=4.5 Hz, 2H), 2.82 (brs, 1H), 3.06 (t, J=4.4 Hz, 2H), 3.08–3.13 (m, 2H), 3.29–3.36 (m, 4H), 3.84 (s, 3H), 6.83–6.96 (m, 4H); IR (KBr, $cm^{-1}$): 3335w;, MS (ES) m/z (relative intensity): 207 ($M^++H$, 100).

Step 7

3-{4-[4-(2-Methoxy-phenyl)-[1,4]diazepan-1-yl]-cyclohexyl}-1H-indole

To 150 mg (0.727 mmol) of 1-(2-methoxy-phenyl)-[1,4] diazepane and 155 mg (0.727 mmol) of 4-(1H-indol-3-yl)-cyclohexanone is added 7 mL of 1,2-dichloroethane, 0.06 mL (66 mg, 1.091 mmol) of HOAc, 231 mg (1.091 mmol) of $NaBH(OAc)_3$ and the resulting mixture was stirred at 23° C. for 19 h. The reaction mixture was then quenched by adding 2 mL of 1N NaOH and poured into saturated aqueous $NaHCO_3$. Extraction with 2×50 mL $CH_2Cl_2$, drying of the combined organics over $Na_2SO_4$, filtration and evaporation gave a yellow oil. Flash chromatography on silica gel, eluting with EtOAc/MeOH:conc. $NH_4OH$ (10/1:0% to 10/1:0.5%) gave 227 mg (0.56 mmol, a 77% yield of the title compound as a white foam. The hydrochloride salt was prepared by dissolving the title compound in 10 mL EtOAc and treating with 0.6 mL (0.6 mmol) of 1M $HCl/Et_2O$. A white solid precipitates from solution and was collected. mp 148–160° C.; IR (KBr, $cm^{-1}$): 3407w, 2529m; MS (ES) m/z (relative intensity): 404 ($M^++H$, 100). Anal. Calcd. for $C_{26}H_{33}N_3O_3 \cdot HCl \cdot C_4H_8O_2 \cdot 2H_2O$: C, 63.87; H, 8.22; N, 7.45. Found: C, 63.87; H, 7.85; N, 8.43.

Example 2

8-{4-[4-(1H-Indol-3-yl)-cyclohexyl]-[1,4]diazepan-1-yl}-quinoline

Step 1

4-Quinolin-8-yl-[1,4]diazepane-1-carboxylic acid tert-butyl ester

The title compound was prepared according to the procedure of Example 1, Step 5 except that 8-bromoquinoline was used in place of 2-bromoanisole. Yield: 68%; $^1H$ NMR (300 MHz, $CDCl_3$): δ1.41 and 1.47 (s, 9H—rotational isomers), 2.05–2.19 (m, 4H), 3.52–3.87 (complex m, 6H), 7.13 (dd, J=1.4, 7.4 Hz, 1H), 7.27–7.41 (m, 3H), 8.07 (d, J=7.4 Hz, 1H), 8.83 (d, J=1.4 Hz, 1H); IR (KBr, $cm^{-1}$): 1689s; MS (ES) m/z (relative intensity): 328 ($M^++H$, 100). Anal. Calcd. for $C_{19}H_{25}N_3O_2$: C, 69.70; H, 7.70; N, 12.83. Found: C, 70.21; H, 7.63; N, 12.17.

Step 2

8-[1,4]Diazepan-1-yl-quinoline

The title compound was prepared according to the procedure of Example 1, Step 6 except that 4-quinolin-8-yl-[1, 4]diazepane-1-carboxylic acid tert-butyl ester was used in place of 4-(2-methoxy-phenyl)-[1,4]diazepane-1-carboxylic acid tert-butyl ester. Yield: 100%; $^1H$ NMR (300 MHz, $CDCl_3$): δ2.05 (pent, J=6.2 Hz, 2H), 3.11 (t, J=5.7, Hz, 2H), 3.31 (t, J=5.6 Hz, 2H), 3.68 (t, J=6.0 Hz, 2H), 3.75 (t, J=6.0 Hz, 2H), 4.47 (brs, 1H), 7.09 (dd, J=1.4, 7.4 Hz, 1H), 7.28–7.39 (m, 3H), 8.02 (dd, J=1.5, 7,5 Hz, 1H), 8.78 (d, J=1.4 Hz, 1H); IR (KBr, $cm^{-1}$): 3309w; MS (ES) m/z (relative intensity): 228 ($M^++H$, 60).

Step 3

8-{4-[4-(1H-Indol-3-yl)-cyclohexyl]-[1,4]diazepan-1-yl}-quinoline

The title compound was prepared according to the procedure of Example 1, Step 7 except that 8-[1,4]diazepan-1- yl-quinoline was used in place of 1-(2-methoxy-phenyl)-[1,4]diazepane. Yield: 65%. The hydrochloride salt was formed according to the procedure of Example 1, Step 7. mp 152–165° C.; IR (KBr, cm$^{-1}$): 3406w, 3245w, 2671; MS (ES) m/z (relative intensity): 425 (M$^+$+H, 100). Anal. Calcd. for $C_{28}H_{32}N_4 \cdot HCl \cdot C_4H_8O_2 \cdot 1.5H_2O$: C, 66.71; H, 7.70; N, 9.72. Found: C, 66.54; H, 7.39; N, 11.19.

Example 3

3-{4-[4-(2-Methoxy-phenyl)-[1,4]diazepan-1-yl]-cyclohexyl}-5-fluoro-1H-indole

Step 1

4-(5-Fluoro-1H-3-indolyl)-cyclohex-3-ene-ethylene ketal

The title compound was prepared according to the procedure of Example 1, Step 1 except that 5-fluroindole was used in place of indole. Yield: 86%. mp 153–155° C.

Step 2

4-(5-Fluoro-1H-3-indolyl)-cyclohexanone ethylene ketal

The title compound was prepared according to the procedure of Example 1, Step 2 except that 4-(5-fluoro-1H-3-indolyl)-cyclohex-3-ene-ethylene ketal was used in place of 3-(1,4-dioxa-spiro[4.5]dec-7-en-8-yl)-1H-indole. Yield: 82%. mp 183–185° C.

Step 3

4-(5-Fluoro-1H-3-indolyl)-cyclohexanone

The title compound was prepared according to the procedure of Example 1, Step 3 except that 4-(5-fluoro-1H-3-indolyl)-cyclohexanone ethylene ketal was used instead of 3-(1,4-dioxa-spiro[4.5]dec-8-yl)-1H-indole. Yield: 91%. mp 112–114° C.

Step 4

3-{4-[4-(2-Methoxy-phenyl)-[1,4]diazepan-1-yl]-cyclohexyl}-5-fluoro-1H-indole 1-(2-Methoxy-phenyl)-[1,4]diazepane (103 mg, 0.5 mmol), 4-(5-fluoro-1H-3-indolyl)-cyclohexanone (116 mg, 0.5 mmol) 5 mL 1,2-dichloroethane and 159 mg (0.75 mmol) of NaBH(OAc), were stirred at 23° C. in a 20 mL scintillation vial for 21 h. The reaction was quenched with 2 mL 1N NaOH, the vial capped, shaken and the organic layer (bottom layer) was removed with an automatic pipet. The organics were removed in a Speed Vac and pumped down overnight to afford 169 mg (0.4 mmol, an 80% yield) of the title compound as an off-white solid. MS (ES) m/z (relative intensity): 422 (M$^+$+H, 100).

Example 4

3-{4-[4-(2-Methoxy-phenyl)-[1,4]diazepan-1-yl-cyclohexyl}-5-cyano-1H-indole

Step 1

4-(5-Cyano-1H-3-indolyl)-cyclohex-3-ene-ethylene ketal

The title compound was prepared according to the procedure of Example 1, Step 1 except that 5-cyanoindole was used in place of indole. Yield: 50%; mp 158–160° C.

Step 2

4-(5-Cyano-1H-3-indolyl)-cyclohexanone ethylene ketal

The title compound was prepared according to the procedure of Example 1, Step 2 except that 4-(5-cyano-1H-3-indolyl)-cyclohex-3-ene-ethylene ketal was used in place of 3-(1,4-dioxa-spiro[4.5]dec-7-en-8-yl)-1H-indole. Yield: 95%; mp 153–155° C.

Step 3

3-(4-Oxo-cyclohexyl)-1H-indole-5-carbonitrile

The title compound was prepared according to the procedure of Example 1, Step 3 except that 4-(5-cyano-1H-3-indolyl)-cyclohexanone ethylene ketal was used instead of 3-(1,4-dioxa-spiro[4.5]dec-8-yl)-1H-indole. Yield: 81%; mp 162–164° C.

Step 4

3-{4-[4-(2-Methoxy-phenyl)-[1,4]diazepan-1-yl]-cyclohexyl}-5-cyano-1H-indole

The title compound was prepared according to the procedure of Example 3, Step 4 except that 3-(4-oxo-cyclohexyl)-1H-indole-5-carbonitrile was used instead of 4-(5-fluoro-1H-3-indolyl)-cyclohexanone. Yield: 60%; MS (ES) m/z (relative intensity): 429 (M$^+$+H, 100).

Example 5

3-{4-[4-(2-Methoxy-phenyl)-[1,4]diazepan-1-yl]-cyclohexyl}-6-fluoro-1H-indole

Step 1

3-(1,4-Dioxa-spiro[4.5]dec-7-en-8-yl)-6-fluoro-1H-indole

The title compound was prepared according to the procedure of Example 1, Step 1 except that 6-fluoroindole was used in place of indole. Yield: 96%; mp 196–197° C.

Step 2

3-(1,4-Dioxa-spiro[4.5]dec-8-yl)-6-fluoro-1H-indole

The title compound was prepared according to the procedure of Example 1, Step 2 except that 3-(1,4-dioxa-spiro[4.5]dec-7-en-8-yl)-6-fluoro-1H-indole was used in place of 3-(1,4-dioxa-spiro[4.5]dec-7-en-8-yl)-1H-indole. Yield: 60%-; mp 183–185° C.

Step 3

4-(6-Fluoro-1H-indol-3-yl)-cyclohexanone

The title compound was prepared according to the procedure of Example 1, Step 3 except that 3-(1,4-dioxa-spiro[4.5]dec-8-yl)-6-fluoro-1H-indole was used instead 3-(1,4-Dioxa-spiro[4.5]dec-8-yl)-1H-indole. Yield: 60%; MS (ES) m/z (relative intensity): 429 (M$^+$+H, 100).

Step 4

3-{4-[4-(2-Methoxy-phenyl)-[1,4]diazepan-1-yl]-cyclohexyl}-6-fluoro-1H-indole

The title compound was prepared according to the procedure of Example 3, Step 4 except that 4-(6-fluoro-1H-3- indolyl)-cyclohexanone ethylene ketal was used instead of 4-(5-fluoro-1H-3-indolyl)-cyclohexanone. Yield: 38% MS (ES) m/z (relative intensity): 422 (M$^+$+H, 100).

Example 6

8-{4-[4-(5-Fluoro-1H-indol-3-yl)-cyclohexyl]-[1,4]diazepan-1-yl}-quinoline

The title compound was prepared according to Example 3, Step 4 except that 8-[1,4]diazepan-1-yl-quinoline is used instead of 1-(2-methoxy-phenyl)-[1,4]diazepane. Yield: 43%; MS (ES) m/z (relative intensity): 443 (M$^+$+H, 100).

Example 7

8-{4-[4-(5-Cyano-1H-indol-3-yl)-cyclohexyl]-[1,4]diazepan-1-yl}-quinoline

The title compound was prepared according to Example 3, Step 4 except that 8-[1,4]diazepan-1-yl-quinoline was used instead of 1-(2-methoxy-phenyl)-[1,4]diazepane and 3-(4-oxo-cyclohexyl)-1H-indole-5-carbonitrile was used in place of 4-(5-fluoro-1H-3-indolyl)-cyclohexanone. Yield: 92%; MS (ES) m/z (relative intensity): 450 (M$^+$+H, 100).

Example 8

8-{4-[4-(6-Fluoro-1H-indol-3-yl)-cyclohexyl]-[1,4]diazepan-1-yl}-quinoline

The title compound was prepared according to Example 3, Step 4 except that 8-[1,4]diazepan-1-yl-quinoline was used instead of 1-(2-methoxy-phenyl)-[1,4]diazepane and 4-(6-fluoro-1H-indol-3-yl)-cyclohexanone was used in place of 4-(5-fluoro-1H-3-indolyl)-cyclohexanone. Yield: 89%; MS (ES) m/z (relative intensity): 443 (M$^+$+H, 100).

Example 9

3-{4-[4-(3-Trifluoromethyl-phenyl)-[1,4]diazepan-1-yl]-cyclohexyl}-5-fluoro-1H-indole

Step 1

4-(3-Trifluoromethyl-phenyl)-[1,4]diazepane-1-carboxylic acid tert-butyl ester

The title compound was prepared according to the procedure of Example 1, Step 5 except that 1-bromo-3-trifluoromethylbenzene was used in place of 2-bromoanisole. Yield: 73%; $^1$H NMR (300 MHz, CDCl$_3$): δ1.33 and 1.43 (s, 9H—rotational isomers), 1.95–2.03 (m, 4H), 3.22 (t, J=4.2 Hz, 2H), 3.34 (t, J=4.2 Hz, 2H), 3.53–3.64 (m, 4H), 6.79–6.91 (m, 2H), 7.25–7.33 (m, 2H); IR (KBr, cm$^{-1}$): 1693s; MS (ES) m/z (relative intensity): 345 (M$^+$+H, 100). Anal. Calcd. for C$_{17}$H$_{23}$F$_3$N$_2$O$_2$: C, 59.29; H, 6.73; N, 8.13. Found: C, 59.24; H, 6.68; N, 8.11.

Step 2

1-(3-Trifluoromethyl-phenyl)-[1,4]diazepane

The title compound was prepared according to the procedure of Example 1, Step 6 except that 4-(3-trifluoromethyl-phenyl)-[1,4]diazepane-1-carboxylic acid tert-butyl ester was used in place of 4-(2-methoxy-phenyl)-[1,4]diazepane-1-carboxylic acid tert-butyl ester. Yield: 91%; $^1$H NMR (300 MHz, CDCl$_3$): δ1.77 (brs, 1H), 1.92 (pent, J=5.9 Hz, 2H), 2.84 (t, J=5.8 Hz, 2H), 3.04 (t, J=5.4 Hz, 2H), 3.56–3.62 (m, 4H), 6.77–6.88 (m, 3H), 7.29 (d, J=7.7 Hz, 1H); IR (KBr, cm$^{-1}$): 3286w; MS (ES) m/z (relative intensity): 245 (M$^+$+H, 60). Anal. Calcd. for C$_{12}$H$_{15}$F$_3$N$_2$: C, 59.01; H, 6.19; N, 11.47. Found: C, 58.56; H, 6.03; N, 10.98.

Step 3

3-{4-[4-(3-Trifluoromethyl-phenyl)-[1,4]diazepan-1-yl]-cyclohexyl}-5-fluoro-1H-indole The title compound was prepared according to Example 3, Step 4 except 1-(3-trifluoromethyl-phenyl)-[1,4]diazepane was used instead of 1-(2-methoxy-phenyl)-[1,4]diazepane. Yield: 86%; MS (ES) m/z (relative intensity): 460 (M$^+$+H, 100).

Example 10

3-{4-[4-(3-Trifluoromethyl-phenyl)-[1,4]diazepan-1-yl]-cyclohexyl)}-5-cyano-1H-indole The title compound was prepared according to Example 3, Step 4 except 1-(3-trifluoromethyl-phenyl)-[1,4]diazepane was used instead of 1-(2-methoxy-phenyl)-[1,4]diazepane and 3-(4-oxo-cyclohexyl)-1H-indole-5-carbonitrile was used in place of 4-(5-fluoro-1H-3-indolyl)-cyclohexanone. Yield: 80%; MS (ES) m/z (relative intensity): 467 (M$^+$+H, 100).

Example 11

3-{4-[4-(3-Trifluoromethyl-phenyl)-[1,4]diazepan-1-yl]-cyclohexyl}-6-fluoro-1H-indole The title compound was prepared according to Example 3, Step 4 except 1-(3-trifluoromethyl-phenyl)-[1,4]diazepane was used instead of 1-(2-methoxy-phenyl)-[1,4]diazepane and 4-(6-fluoro-1H-indol-3-yl)-cyclohexanone was used in place of 4-(5-fluoro-1H-3-indolyl)-cyclohexanone. Yield: 64%; MS (ES) m/z (relative intensity): 460 (M$^+$+H, 100).

What is claimed is:

1. A compound of the formula:

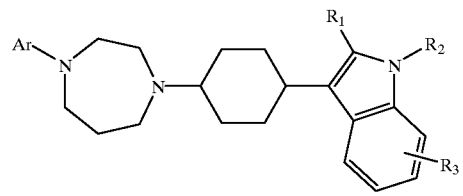

wherein:

Ar is an aryl group of 4 to 10 carbon atoms, or a heteroaryl group of 4 to 10 ring atoms having 1–3 ring heteroatoms each of which is N;

$R_1$ and $R_2$ are independently selected from hydrogen, straight chain alkyl of 1 to 12 carbon atoms, branched alkyls of 3 to 10 carbon atoms or cycloalkyl of 3 to 10 carbon atoms;

$R_3$ is H, straight chain alkyl of 1 to 12 carbon atoms, branched alkyl of 3 to 10 carbon atoms, cycloalkyl of 3 to 10 carbon atoms, halogen, alkoxy group of 1 to 12 carbon atoms, haloalkyl of 1 to 12 carbon atoms, hydroxy, nitro, nitrile, amino, cyano, carboxy, alkoxycarbonyl of 1 to 12 carbon atoms, alkylcarbonyl of 1 to 12 carbon atoms, aminocarbonyl and alkylaminocarbonyl of 1 to 12 carbon atoms; or a pharmaceutically acceptable salt thereof.

2. A compound according to claim 1 of formula I wherein:

Ar is an aryl group of 5 or 6 carbon atoms or a heteroaryl group of 5 to 10 ring atoms;

$R_1$ and $R_2$ are independently, H, straight chain alkyls of 1 to 8 carbons or branched alkyls of 3 to 8 carbon atoms;

$R_3$ is H, straight chain alkyl of 1 to 8 carbon atoms, branched alkyl of 3 to 6 carbon atoms, cycloalkyl of 3 to 8 carbon atoms, halogen, alkoxy of 1 to 6 carbon atoms, haloalkyl of 1 to 6 carbon atoms, haloalkoxy or 1 to 6 carbon atoms, hydroxy, nitro, nitrile, amino, cyano, carboxy, alkoxycarbonyl of 1 to 6 carbon atoms, alkylcarbonyl of 1 to 6 carbon atoms, aminocarbonyl and alkylaminocarbonyl of 1 to 6 carbon atoms; or a pharmaceutically acceptable salt thereof.

3. A compound according to claim 1 of formula I wherein:

Ar is an aryl group of 6 carbon atoms or a heteroaryl group of 5 to 10 ring atoms;

$R_1$ and $R_2$, are independently, H, straight chain alkyls of 1 to 3 carbons or branched alkyls of 3 to 6 carbon atoms;

$R_3$ is H, halogen, cyano $CONH_2$, or $CO_2H$;

or a pharmaceutically acceptable salt thereof.

4. A compound of claim 1 wherein Ar is selected from phenyl, benzyl, naphthalene, anthracene, phenanthrene, indene or indacene, each optionally substituted by from 1 to 3 groups selected from alkyl of 1 to 12 carbon atoms, —$CF_3$, alkoxy of 1 to 12 carbon atoms, and halogen.

5. A compound of claim 1 wherein Ar is selected from pyridine, pyrimidine, pyrrole, imidazole, pyrazole, triazole, quinolizine, quinoline, and isoquinoline, each optionally substituted by from 1 to 3 groups selected from alkyl of 1 to 12 carbon atoms, —$CF_3$, alkoxy of 1 to 12 carbon atoms, and halogen.

6. A compound of claim 1 which is 3-{4-[4-(2-methoxyphenyl)-[1,4]diazepan-1-yl]-cyclohexyl}-1H-indole or a pharmaceutically acceptable salt thereof.

7. A compound of claim 1 which is 8-{4-[4-(1H-indol-3-yl)-cyclohexyl]-[1,4]diazepan-1-yl}-quinoline or a pharmaceutically acceptable salt thereof.

8. A compound of claim 1 which is 3-{4-[4-(2-methoxyphenyl)-[1,4]diazepan-1-yl]-cyclohexyl}-5-fluoro-1H-indole or a pharmaceutically acceptable salt thereof.

9. A compound of claim 1 which is 3-{4-[4-(2-methoxyphenyl)-[1,4]diazepan-1-yl]-cyclohexyl}-5-cyano-1H-indole or a pharmaceutically acceptable salt thereof.

10. A compound of claim 1 which is 3-{4-[4-(2-methoxyphenyl)-[1,4]diazepan-1-yl]-cyclohexyl}-6-fluoro-1H-indole or a pharmaceutically acceptable salt thereof.

11. A compound of claim 1 which is 8-{4-[4-(5-fluoro-1H-indol-3-yl)-cyclohexyl]-[1,4]diazepan-1-yl}-quinoline or a pharmaceutically acceptable salt thereof.

12. A compound of claim 1 which is 8-{4-[4-(5-cyano-1H-indol-3-yl)-cyclohexyl]-[1,4]diazepan-1-yl}-quinoline or a pharmaceutically acceptable salt thereof.

13. A compound of claim 1 which is 8-{4-[4-(6-fluoro-1H-indol-3-yl)-cyclohexyl-]-[1,4]diazepan-1-yl}-quinoline or a pharmaceutically acceptable salt thereof.

14. A compound of claim 1 which is 3-{4-[4-(3-trifluoromethyl-phenyl)-[1,4]diazepan-1-yl]-cyclohexyl}-5-fluoro-1H-indole or a pharmaceutically acceptable salt thereof.

15. A compound of claim 1 which is 3-{4-[4-(3-trifluoromethyl-phenyl)-[1,4]diazepan-1-yl]-cyclohexyl}-5-cyano-1H-indole or a pharmaceutically acceptable salt thereof.

16. A compound of claim 1 which is 3-{4-[4-(3-trifluoromethyl-phenyl)-[1,4]diazepan-1-yl]-cyclohexyl}-6-fluoro-1H-indole or a pharmaceutically acceptable salt thereof.

17. A pharmaceutical composition comprising a compound of claim 1, or a pharmaceutically acceptable salt thereof, and a pharmaceutically acceptable carrier or excipient.

18. A method of treating depression in a mammal, the method comprising administering to a mammal in need thereof a pharmaceutically effective amount of a compound of claim 1, or a pharmaceutically acceptable salt thereof.

19. A method of treating anxiety in a mammal, the method comprising administering to a mammal in need thereof a pharmaceutically effective amount of a compound of claim 1, or a pharmaceutically acceptable salt thereof.

* * * * *